United States Patent [19]

Kane

[11] Patent Number: 4,624,266

[45] Date of Patent: Nov. 25, 1986

[54] INTRODUCER TOOL FOR SCREW-IN LEAD

[75] Inventor: Lawrence M. Kane, Roseville, Minn.

[73] Assignee: Daig Corporation, Minnetonka, Minn.

[21] Appl. No.: 562,830

[22] Filed: Dec. 19, 1983

[51] Int. Cl.⁴ ............................................. A61N 1/05
[52] U.S. Cl. ................................. 128/785; 128/419 P
[58] Field of Search ............................... 128/784–786, 128/419 P, 642

[56] References Cited

U.S. PATENT DOCUMENTS

| | | | |
|---|---|---|---|
| 3,951,154 | 4/1976 | Hartlaub | 128/419 |
| 4,103,690 | 8/1978 | Harris | 128/786 X |
| 4,209,019 | 6/1980 | Dutcher et al. | 128/419 P |
| 4,253,462 | 3/1981 | Dutcher et al. | 128/303 |
| 4,257,429 | 3/1981 | Dickhudt et al. | 128/786 |
| 4,311,153 | 1/1982 | Smits | 128/785 |
| 4,350,169 | 9/1982 | Dutcher et al. | 128/783 |
| 4,381,013 | 4/1983 | Dutcher | 128/785 |
| 4,570,642 | 2/1986 | Kane et al.a | 128/785 |

Primary Examiner—Lee S. Cohen
Attorney, Agent, or Firm—Herman H. Bains; Malcolm L. Moore; Conrad A. Hansen

[57] ABSTRACT

A stylet and introducer tool is used with a screw-in electrode which is adapted to attach living tissue to a pulse generator, such as a pacemaker or the like. The stylet has a knob at its proximal end and extends through the introducer tool and coiled conductor of the lead to engage a helix assembly positioned within the hollow electrode of the lead. The stylet is adapted to urge the helix of the helix assembly into contact with the living tissue. The knob of the stylet engages in a slot in the introducer tool to lock the stylet to the introducer tool and permit the screw-in lead to be rotated around the stylet so that the helix will penetrate the living tissue.

7 Claims, 3 Drawing Figures

U.S. Patent   Nov. 25, 1986   4,624,266
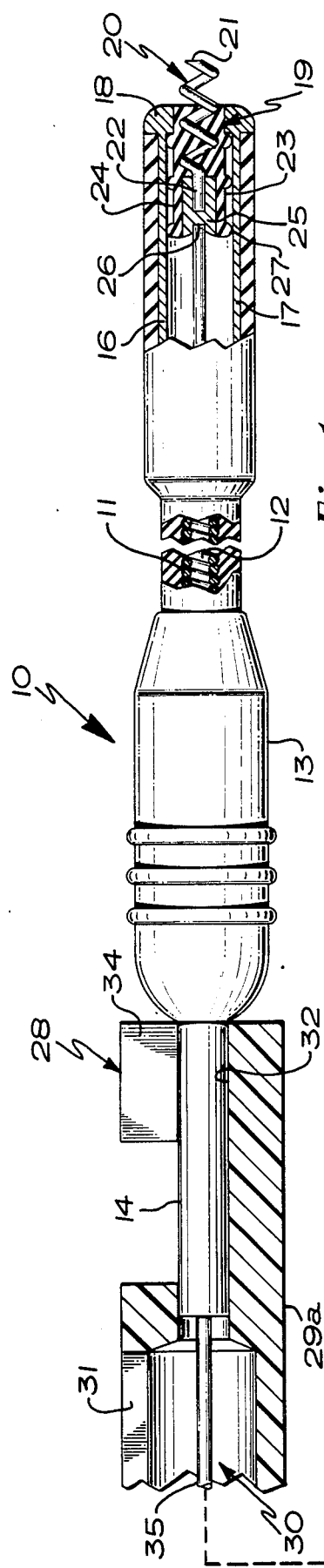
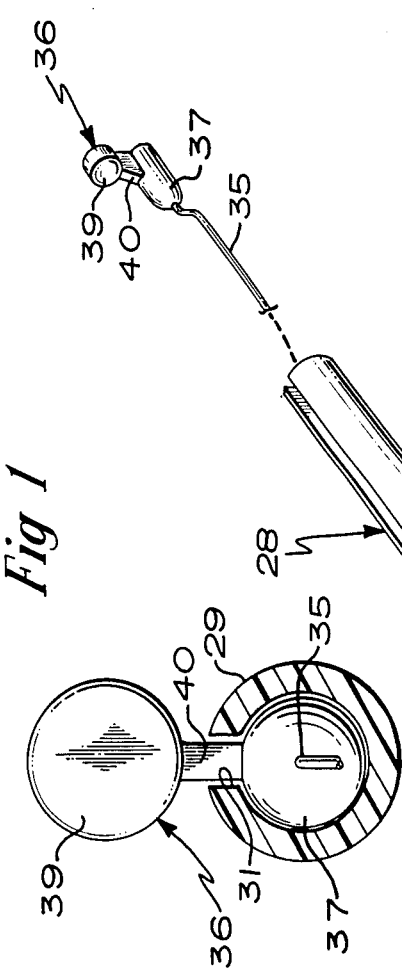
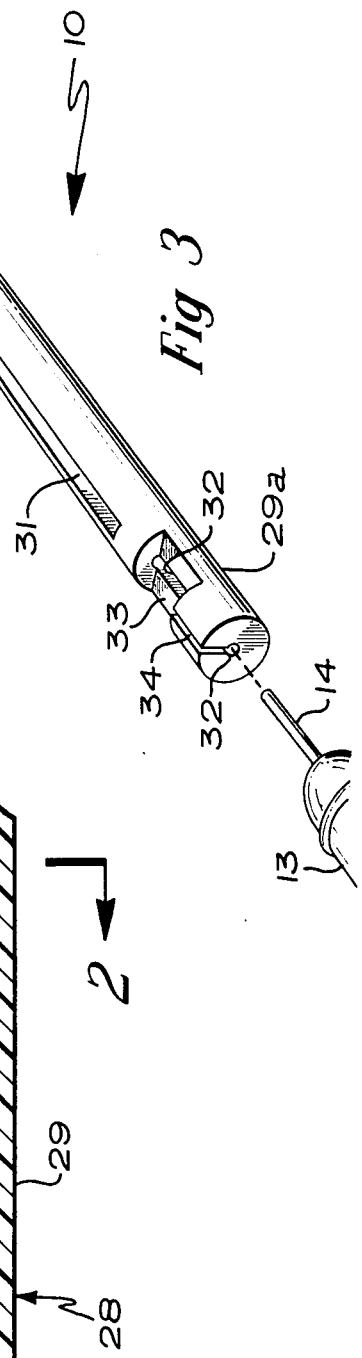
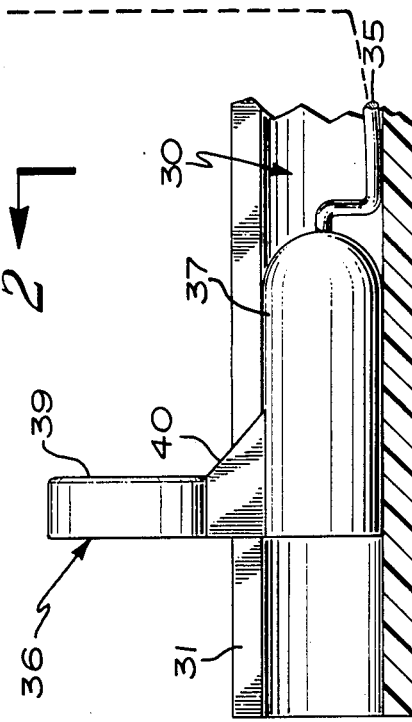

INTRODUCER TOOL FOR SCREW-IN LEAD

BACKGROUND OF THE INVENTION

This invention relates to a lead for connecting tissue to an electrical pulse generator, and more particularly to an introducer tool for use with an endocardial lead having a helical fixation element.

The screw-in concept has long been known as a viable means for achieving positive fixation in atrial and ventricular pacing applications. A screw-in lead is illustrated in my co-pending application entitled ENDOCARDIAL EXTENDABLE SCREW-IN LEAD by Lawrence M. Kane and James E. Revane, Ser. No. 535,318. The screw-in lead in my co-pending application is provided with an introducer tool which facilitates the introduction of the lead into the heart, and is essential in the fixation of the helical element in the cardiac tissue. The present invention is directed to a novel and improved introducer tool for use with the introduction of the lead and the fixation of the helical element to the tissue.

SUMMARY OF THE INVENTION

It is a general object of this invention to provide a novel and improved introducer tool for a screw-in lead which permits a doctor to use a single hand for active fixation of the screw-in helix into the body tissue.

Another object of this invention is to provide a novel and improved introducer tool for an endocardial lead which is of simple and efficient construction.

These and other objects and advantages of the invention will appear more fully from the following description made in conjunction with the accompanying drawings wherein like reference characters refer to the same or similar parts throughout the several views.

FIGURES OF THE DRAWING

FIG. 1 is a side view, partly in section and partly in elevation, foreshortened, with certain parts thereof broken away for clarity;

FIG. 2 is a cross-sectional view taken approximately along line 2—2 of FIG. 1 and looking in the direction of the arrows; and FIG. 3 is an exploded perspective view of the novel introducer tool.

DESCRIPTION OF THE PREFERRED EMBODIMENT

Referring now to the drawings, it will be seen that one embodiment of an intravascular lead, designated generally by the reference numeral 10, is thereshown. The endocardial lead illustrated is identical to that shown in my co-pending application entitled ENDOCARDIAL EXTENDABLE SCREW-IN LEAD, filed Sept. 23, 1983, Ser. No. 535,318, now U.S. Pat. No. 4,570,642 and the disclosure thereof is incorporated herein by reference. It is pointed out that the lead 10 may be of unipolar configuration, as shown, or may be of bipolar configuration, as is well known in the art. The endocardial lead 10 includes a coil conductor 11 formed of a nickel alloy wire, and the coil conductor defines a lumen 12. The conductor is covered with a sleeve or jacket 13 of electrically insulating material, namely silicone rubber.

The proximal end of the conductor 11 is connected to a tubular pin connector 14 which is adapted for insertion in a receptacle provided on a pulse generator with which the lead is used. It will be noted that the connector pin 14 is embedded in a silicone catheter sleeve 13 and projects therefrom. The particular construction of the connector pin end is illustrated in detail in my co-pending application. The distal end of the coil conductor 11 is electrically connected to an elongate, cylindrical, ring tip electrode 16 which is formed of platinum iridium alloy. The precise manner of connection of the coil conductor 11 to the electrode 16 is also illustrated in detail in my co-pending application. The electrode 16 includes a sleeve or barrel 17 provided with an outwardly projecting, annular lip 18 at its distal end.

A helix assembly 19 is positioned within the barrel 17 of the electrode, and includes a helical element 20, which is also formed of platinum iridium material, and which has a point 21 at its distal end and a straight shank portion 22 at its proximal end. It will be seen that an intermediate portion of the helical element 20 is embedded in a cylindrical sealing member 23, which is formed of silicone, so that the distal portion of the helical element 20 projects axially from the end of the sealing member. The sealing member 23 has a rearwardly facing, axially extending recess 24 therein which accommodates a metallic anchoring element 25 therein. The anchoring element 25 has a rearwardly facing recess 26 therein which accommodates a stylet in a manner to be described more fully herein below.

The sealing member also has a plurality of axially spaced apart, annular sealing elements 27 which project radially outwardly therefrom. Again it is pointed out that the helix assembly is identical to that set forth in my co-pending application, Ser. No. 535,318. It is also pointed out that the radial dimension of each annular sealing element 27 is such that the sealing elements 27 engage the inner surface of the electrode barrel in sealing, frictional engagement. This frictional contact permits forcible longitudinal movement of the helix assembly, but prevents rotation of the helix assembly relative to the electrode 16.

It is also pointed out that the helix assembly 19 is in the retracted position when the lead is introduced into the vein, and subsequently into the heart chamber. Thereafter, the helix assembly is advanced with the stylet, and the lead is thereafter affixed to the cardiac tissue.

A stylet is used to shift the helix assembly from the retracted position to the extended position. The stylet cooperates with an introducer tool 28 which is formed of a rigid plastic material, and includes an elongate, cylindrical stylet guide portion 29 and a connector pin engaging portion 29a. It will be noted that the stylet guide portion 29 extends from the distal end of the introducer tool 28, and includes a major portion of the length of the introducer tool.

The connector pin engaging portion 29a extends from the distal end of the introducer tool and has a length dimension substantially less than the length dimension of the stylet guide portion 29. The stylet guide portion 29 has a uniform cylindrical bore 30 therethrough which extends from the proximal end of the stylet guide portion to the connector pin engaging portion 29a. An elongate slot 31 in the stylet guide portion 29 communicates with the bore 30 and corresponds in length to approximately the length of the bore 30.

The connector pin engaging portion 29 has a smaller cylindrical uniform bore 32 therethrough which extends from the distal end of the introducer tool and communicates with the bore 30. The connector pin engaging portion 29a also has a semicircular notch 33 therein that communicates with the bore 32 therein. The distal end portion of the connector pin engaging portion 29a also has a radial slot 34 therein that communicates with the bore 32 and with the semicircular notch 33.

The introducer tool 28 is adapted to accommodate an elongate stylet 35 formed of a stainless steel wire, and having a knob 36 on its proximal end. The stylet 35, when applied to the introducer tool 28, extends through the cylindrical bore 30 and through the reduced bore 32 in the connector pin engaging portion 29a. The connector pin engaging portion 29a is adapted to receive the connector pin 14 therein. When the connector pin projects into the bore 32, it will be seen that a portion thereof projects into the notch 33.

The stylet knob 36 includes a generally cylindrical base member 37. It is pointed out that the stylet knob 36 is formed of a plastic material similar to that of the introducer tool 28, and includes a finger engaging portion 39 which is of circular configuration and which is disposed in a plane substantially normal to the longitudinal axis of the introducer tool 28. The finger engaging portion 39 is connected to the base member 37 by a connector portion 40 which projects through the slot 31.

In the procedure for attaching the lead to the cardiac tissue, the helix assembly will be in the retracted position and the distal end of the stylet will be moved forwardly by the physician until the distal end of the stylet merely engages in the recess 26 in the anchoring element 25. After the lead has been passed through the superior vena cava vein into the right atrium, or into the right ventricle, the physician will map the area by connecting an oscilloscope or other monitoring device between the connector pin 14 on the lead and ground. Again it will be appreciated that a suitable electrical connector clip may be applied to that portion of the connector pin positioned within the notch 33. Once an acceptable position for attachment is found, the stylet knob and stylet will be urged into the lead a distance of approximately two or three inches, which causes the helix assembly 19 to be shifted longitudinally of the electrode barrel until the helix assembly reaches the fully extended position, as illustrated in FIG. 1. The physician will retain the stylet in this position until the helix is clearly visible on the fluoroscopy monitor.

After the helix assembly has been moved to the extended position, the stylet 35 may now be moved proximally a few inches so that the tension is released in the lead. The physician may then grip the introducer tool and the proximal end of the lead with one hand and rotate the lead jacket with thumb and forefinger, including the coil conductor and helix assembly, in a clockwise direction approximately six turns to engage the endocardium with the corkscrew helical element. The stylet 35 will then be retracted an additional three or four inches and slight tension will thereafter be applied to the lead 10 to verify fixation by observation with the fluoroscopy unit. After verification of fixation, the stylet may then be removed from the lead and the introducer tool will then be disengaged and removed from the connector lead.

The present construction and operation of the introducer tool 28 provides the extremely important advantage of permitting the physician to grip the introducer tool and rotate the lead relative to the introducer tool with a single hand, thereby allowing the physician to use his other hand to perform other tasks involved in this procedure.

It will also be noted that the novel introducer tool also positively grips the connector pin of the lead while exposing the connector pin for ready electrical connection to a monitoring unit.

Thus it will be seen that I have provided a novel introducer tool for a screw-in type lead for cardiac pacemakers, which is not only of simple construction, but one which functions in a more efficient manner than any heretofore known comparable introducer tool.

While the preferred embodiments of the present invention have been described, it should be understood that various changes, adaptions and modifications may be made therein without departing from the spirit of the invention and the scope of the appended claims.

What is claimed is:

1. An introducer tool and styet in combination with an intravascular lead formed of a material inert to body fluids and adapted to be connected to a body tissue, said lead including an electrically insulated flexible coil conductor having a lumen therethrough and having proximal and distal ends, a connector pin electrically connected to the proximal end of the conductor and a hollow electrode connected to the distal end of the conductor and adapted to contact the body tissue, a helix assembly in the electrode including a non-conductive sealing member engaging the interior of the electrode, a helical element secured to the sealing member and projecting therefrom, the helix assembly being shiftable from a retracted position wherein the helical element is disposed completely within the electrode, and an extended position wherein the helical element projects outwardly of the electrode, said introducer tool comprising an elongated body having a longitudinally extending opening therethrough and detachably engaging said connector pin to secure the introducer tool to the lead but permitting rotation of the later relative to the introducer tool;

said stylet comprising an elongated wire-like member having proximal and distal ends and being inserttable into the opening in the introducer tool and the lumen of the conductor and engaging the helix assembly and non-rotatably shifting the same in a longitudinal direction from the retracted position to the extended position, cooperating means on said stylet and said introducer tool permitting longitudinal insertion and retraction of the stylet relative to the introducer tool, but locking the stylet against rotation relative to the introducer tool whereby when the helix assembly is in the extended position and the conductor, electrode and helix assembly are rotated as a unit about the stylet, the helix assembly will penetrate the cardiac tissue and urge the electrode into positive engagement with the tissue.

2. The invention as defined in claim 1 wherein said introducer tool has proximal and distal ends and includes a stylet guide portion extending in a distal direction from the proximal end thereof, and a connector pin engaging portion extending in a proximal direction from the distal end thereof, said opening in said introducer tool extending through said stylet guide portion and said connector pin engaging portion, said cooperating means on said stylet and introducer tool including a slot in said stylet guide portion communicating with said opening, and a knob on the proximal end of said stylet and engaging in said slot to permit longitudinal movement of said stylet, but locking the latter against rotation relative to said introducer tool.

3. The invention as defined in claim 2 wherein said opening through the connector pin engaging portion in said introducer tool is smaller in cross-sectional size than the cross-sectional size of the opening through the stylet guide portion.

4. The invention as defined in claim 3 wherein said connector pin engaging portion has a longitudinally extending slot therein communicating with the opening therein to facilitate gripping of the connector pin by said connector pin engaging portion.

5. The invention as defined in claim 2 and a notch in said connector pin engaging portion communicating with said opening therein to expose a portion of the connector pin when the latter projects into said connector pin engaging portion to thereby permit an electrical clip to be applied to said connector pin.

6. The invention as defined in claim 2 wherein said knob on said stylet includes a finger engaging portion and a base portion, said base portion being positioned within the opening in said stylet guide portion and said finger engaging portion being connected with said base portion and projecting through said slot exteriorly of the introducer toll.

7. The invention as defined in claim 2 wherein said introducer tool is of cylindrical configuration.

* * * * *

UNITED STATES PATENT AND TRADEMARK OFFICE
CERTIFICATE OF CORRECTION

PATENT NO. : 4,624,266
DATED : November 25, 1986
INVENTOR(S) : Lawrence M. Kane

It is certified that error appears in the above-identified patent and that said Letters Patent are hereby corrected as shown below:

In claim 6, line 13, change "toll" to --tool--.

Signed and Sealed this

Third Day of March, 1987

*Attest:*

DONALD J. QUIGG

*Attesting Officer*   *Commissioner of Patents and Trademarks*